(12) United States Patent
Lee

(10) Patent No.: US 6,555,798 B1
(45) Date of Patent: Apr. 29, 2003

(54) HEATING APPARATUS OF HOT-HEAT TREATMENT DEVICE USING SEMICONDUCTOR DEVICE

(75) Inventor: Sang-bok Lee, Taejon (KR)

(73) Assignee: Migun Medical Instrument Co., Ltd. (KR)

(*) Notice: Subject to any disclaimer, the term of this patent is extended or adjusted under 35 U.S.C. 154(b) by 65 days.

(21) Appl. No.: 09/722,679

(22) Filed: Nov. 28, 2000

(30) Foreign Application Priority Data

Dec. 3, 1999 (KR) .............................. 99-54662

(51) Int. Cl.[7] ................. H05B 3/00; A61F 7/08
(52) U.S. Cl. ................... 219/527; 219/530; 607/96
(58) Field of Search ............................ 219/527, 528, 219/549, 505, 530, 540; 607/96

(56) References Cited

U.S. PATENT DOCUMENTS

| 2,018,512 A | * | 10/1935 | Delaney et al. ............. 219/528 |
| 4,937,435 A | * | 6/1990 | Goss et al. .................. 219/528 |
| 5,720,774 A | * | 2/1998 | Glucksman .................. 607/96 |
| 6,187,029 B1 | * | 2/2001 | Shapiro et al. ................ 607/88 |

FOREIGN PATENT DOCUMENTS

| KR | 84-967 U | 3/1984 |
| KR | 95-4672 U | 2/1995 |

* cited by examiner

Primary Examiner—John A. Jeffery
(74) Attorney, Agent, or Firm—Rothwell, Figg, Ernst & Manbeck

(57) ABSTRACT

A heating apparatus of a hot-heat treatment device using a semiconductor device includes a heating element positioned in a heating cap for heating a transmission cover after being conducted when electric power is supplied thereto; a circuit board electrically connected with the heating element, for controlling a voltage and a temperature; and a fixing unit for integrally fixing the heating element within the heating cap. Since the light bulb in the heating structure of the heating cap for pressurizing and fomenting the diseased part of the body of the user as in the conventional art is replaced with a semiconductor device. Accordingly, its case is prevented from deforming and the lead wire is prevented from breaking due to heat, so that a high-quality product can be provided.

4 Claims, 2 Drawing Sheets

US 6,555,798 B1

HEATING APPARATUS OF HOT-HEAT TREATMENT DEVICE USING SEMICONDUCTOR DEVICE

BACKGROUND OF THE INVENTION

1. Field of the Invention

The present invention relates to heating apparatus of a hot-heat treatment device using a semiconductor device, and more particularly, to a heating apparatus of a hot-heat treatment device using a semiconductor device which is capable of reducing the number of calling for after-service by replacing a heating structure in a heating cap for pressurizing and fomenting a diseased part of the body of a user with a semiconductor device, and capable of preventing a case from deforming and a lead wire from breaking, caused due to heat, to thereby provide a high quality product.

2. Description of the Background Art

A general hot-heat treatment device is to pressurize and foment a diseased part of a body of a user by using a Helium lamp or an infrared lamp. The general hot-heat treatment device largely includes a controller for controlling all parts, and a main body electrically connected with the controller to operate a treatment lamp. And, to facilitate movement and keeping in view of a characteristic of the hot-heat treatment device, there is also provided a bag to hold the hot-heat treatment device, the controller and the peripheral parts.

FIG. 1 is a vertical-sectional view of a general hot-heat treatment device in accordance with a conventional art.

As shown in the drawing, the conventional hot-heat treatment device includes a treatment lamp 30 electrically connected with a socket 31 installed in a lower case 12, an upper case 11 having a combining groove 14 at a position corresponding to a treatment lamp 30 and being combined with the lower case 12, and a transmission cover 20 inserted into the combining groove 14 of the upper case 11 in a manner that its upper end portion is exposed and having transmission holes 21 to emit light and heat generated by the treatment lamp 30.

In case where the conventional hot-heat treatment device constructed as described above is desired to use, the controller is electrically connected and electric power is applied thereto. Then, intrinsic light and wave length are radiated from the treatment lamp 30. The light heats the transmission cover 20 as well as being radiated through the transmission holes 21. Then, the user positions the hot-heat treatment device on a diseased part of the body, for fomenting it.

However, the conventional hot-heat treatment device has the following 15 shortcomings. That is, since it utilizes the treatment lamp, that is, a light bulb, for heating, if the treatment lamp is used for a long period of time, it is easily damaged, causing an inconvenience of repairing it by after-service. In addition, due to the hot heat radiated from the treatment lamp 30, its lead wire may be broken or the case may be deformed.

SUMMARY OF THE INVENTION

Therefore, an object of the present invention is to provide to a heating apparatus of a hot-heat treatment device using a semiconductor device which is capable of reducing the number of calling for after-service by replacing a heating structure of a heating cap for pressurizing and fomenting a diseased part of a user with a semiconductor device, and capable of preventing a case from deforming and a lead wire from breaking, caused due to heat, to thereby provide a high-quality product.

To achieve these and other advantages and in accordance with the purpose of the present invention, as embodied and broadly described herein, there is provided a heating apparatus of a hot-heat treatment device using a semiconductor device including: a heating element positioned in a heating cap for heating a transmission cover after being conducted when electric power is supplied thereto; a circuit board electrically connected with the heating element, for controlling a voltage and a temperature; and a fixing unit for integrally fixing the heating element within the heating cap.

A PTC (Positive Temperature Coefficient) semiconductor device, that is, the heating element, is a kind of an n-type semiconductor device that a very small amount of rare earth element is added to $BatiO_3$, that is, a principal component, to have electric conductivity, of which a part of Ba may be replaced with Sr or Pb for change of its Curie temperature. The PTC semiconductor device is known to have a characteristic that when it reaches a temperature, the temperature rapidly goes up due to a phase transition and its resistance value is rapidly increased accordingly.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1A:
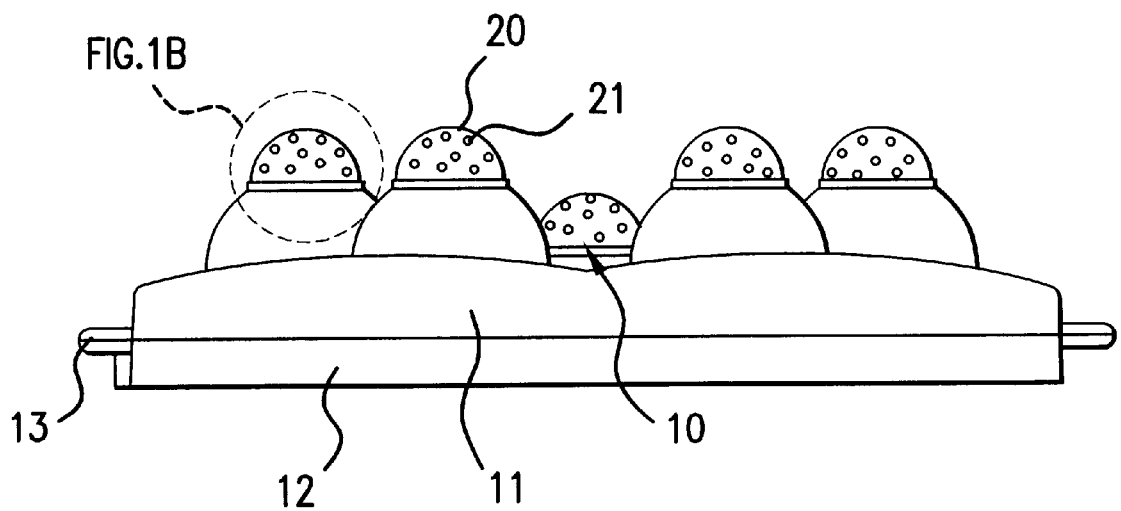
FIG. 1A is a vertical-sectional view of a hot-heat treatment device in accordance with a conventional art.
Figure 1B:
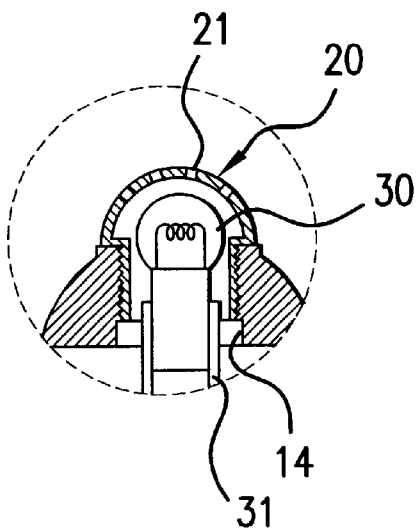
FIG. 1B is an inset of the device shown in FIG. 1A.
Figure 2A:
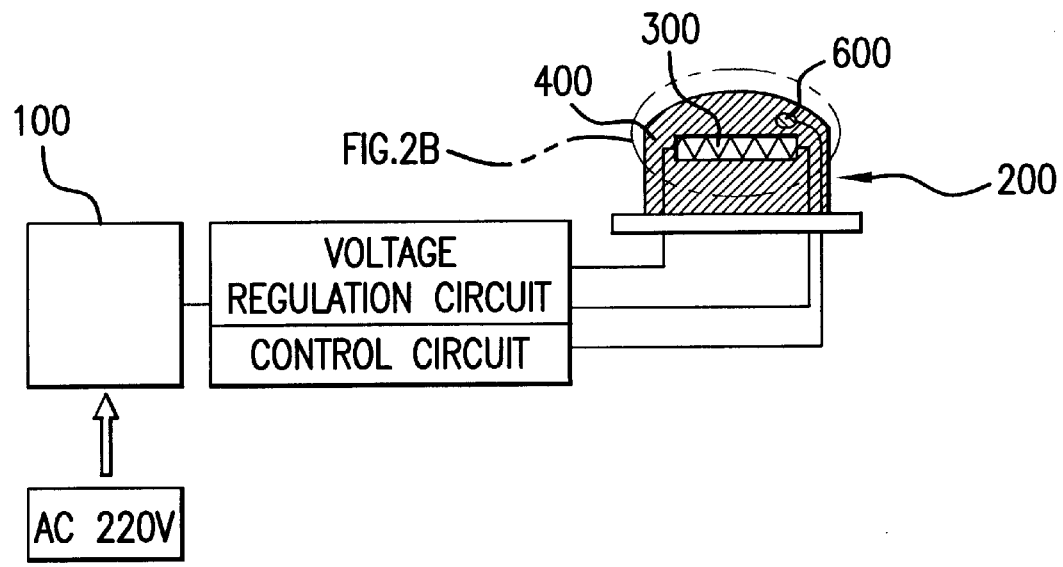
FIG. 2A shows a construction of a heating apparatus in accordance with an embodiment of the present invention.
Figure 2B:
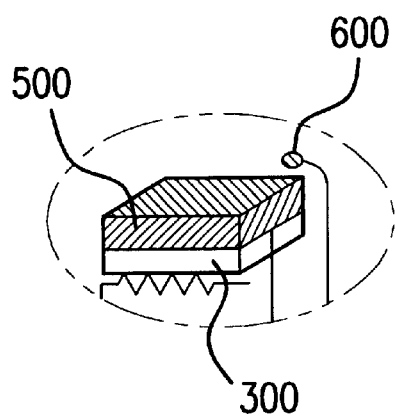
FIG. 2B is an inset of the embodiment shown in FIG. 2A.

FIG. 2 shows a construction of a heating apparatus in accordance with the present invention.

As shown in the drawing, the heating apparatus of a hot-heat treatment device using a semiconductor device includes: a heating element 300 positioned in a heating cap 200 for heating a the heating cap 200 after being conducted when electric power is supplied thereto; a circuit board 100 electrically connected with the heating element 300, for controlling a voltage and a temperature; and a fixing unit 400 for integrally fixing the heating element 300 within the heating cap 200.

The heating element 300, made of a PTC semiconductor, includes heating plates stacked at the upper portion thereof. Thus, heat is transmitted upwardly and the lead wire is prevented from breaking. In the vicinity of the heating element 300, there is formed a temperature sensor 600 for sensing a temperature of the heating element.

The fixing unit 400 is formed by selectively coating silicon grease or heat-resistant epoxy which is resistant to an impact or a vibration, so that it's original form is maintained for a certain degree of impact. As a material for the heating cap 200, mineral substance is selected.

In case where the heating apparatus of a hot-heat treatment device using a semiconductor device of the present invention is desired to use, when the hot-heat treatment device is operated, the heating element 300 is electrically operated and heated at a certain temperature, and the heat is transmitted upwardly through the heating plates 500, heating the heating cap 200.

At this time, the temperature sensor 600 senses a proper temperature of the heating element 300 and the sensed temperature is controlled by a control circuit.

As so far described, according to the heating apparatus of a hot-heat treatment device using a semiconductor device of the present invention, since the light bulb in the heating structure of the heating cap for pressurizing and fomenting the diseased part of the body of the user as in the conventional art is replaced with a semiconductor device. Accordingly, its case is prevented from deforming and the lead wire is prevented from breaking due to heat, so that a high-quality product can be provided.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A heating apparatus of a hot-heat treatment device using a semiconductor device comprising:

a heating element positioned in a heating cap for heating the heating cap after being conducted when electric power is supplied thereto;

a circuit board electrically connected with the heating element, for controlling a voltage and a temperature; and a fixing unit for integrally fixing the heating element with the heating cap;

wherein the fixing unit is formed by coating silicon grease or heat-resistant epoxy.

2. The heating apparatus according to claim 1, wherein the heating element is made of a PTC semiconductor.

3. The heating apparatus according to claim 1, wherein heating plates are formed stacked in the heating element.

4. The heating apparatus according to claim 3, wherein the heating plates are formed only at the upper portion of the heating element.

* * * * *